United States Patent [19]

Jubin, Jr.

[11] Patent Number: 4,751,055
[45] Date of Patent: Jun. 14, 1988

[54] FIXED BED REACTOR SYSTEM

[75] Inventor: John C. Jubin, Jr., Wallingford, Pa.

[73] Assignee: Atlantic Richfield Company, Los Angeles, Calif.

[21] Appl. No.: 799,066

[22] Filed: Nov. 18, 1985

Related U.S. Application Data

[62] Division of Ser. No. 601,143, Apr. 16, 1984.

[51] Int. Cl.$^4$ ............................................. B01J 8/04
[52] U.S. Cl. ................................. 422/190; 422/192; 422/194; 422/211; 422/223
[58] Field of Search ............... 422/192, 194, 190, 211, 422/223

[56] References Cited

U.S. PATENT DOCUMENTS

| | | | |
|---|---|---|---|
| 2,310,244 | 2/1943 | Lassiat | 422/190 |
| 2,475,855 | 7/1949 | Peters | 422/192 |
| 3,982,903 | 9/1976 | Anderson | 422/211 |
| 4,259,294 | 3/1981 | Langhout | 422/190 |

*Primary Examiner*—Kenneth M. Schor
*Assistant Examiner*—Lori Ann Cody
*Attorney, Agent, or Firm*—Craig E. Larson

[57] ABSTRACT

An apparatus is disclosed in which a first gas is contacted with a solid at an elevated reaction temperature to produce a gaseous product, the solid being deactivated during said contact and exothermically reactivated by a second gas and again contacted with the first gas, the improvement includes the steps of:

(a) providing a quantity of the solids in relatively equal amounts to at least these fixed bed reactors;

(b) sequentially operating each fixed bed reactor according to the cycle comprising: (1) preheating introducing the first gas into a first end of the reactor and withdrawing gaseous product from a second end of the reactor; (2) preheating the first gas to reaction temperature by introducing the first gas into the fixed bed of solids at a plurality of points along the length of the reactor and withdrawing the preheated gas from the second end of the reactor; and (3) reactivating the deactivated solids by introducing the second gas into the fixed bed of solids at a plurality of points along the length of the reactor and withdrawing second gas effluent from the first end of the reactor; and (c) concurrently operating the reactors such that, at any given time, the first gas is being preheated to reaction temperature in at least one reactor, and the preheated first gas is being converted into second gas in at least one second reactor.

2 Claims, 6 Drawing Sheets

FIXED BED REACTOR SYSTEM

This is a division of application Ser. No. 601,143, filed Apr. 16, 1984.

BACKGROUND OF THE INVENTION

1. Field of the Invention

This invention relates to chemical conversions that involve processes wherein solids and fluids are contacted to effect the desired conversion. More particularly, this invention relates to chemical conversion of gaseous hydrocarbons over fixed beds of solids. One particular embodiment of this invention relates to the synthesis of hydrocarbons from a methane source. Another particular embodiment of this invention relates to dehydrogenation of hydrocarbons. This invention also relates to a novel, multi-reactor, fixed bed, gas-solid contacting system.

2. Fixed Bed Reactor Systems

A wide variety of chemical conversions are known wherein fluid reactants are contacted with solids, the solids either functioning as catalysts to promote the conversion of reactants to desired products or functioning as a reactant (or both). Typically, the solids in such processes, whether functioning as catalysts or as reactants, require periodic replenishment or regeneration.

A preferred means for conducting many such industrial chemical processes involves the use fluidized beds of solids with circulation of solids between reaction and regeneration zones. While ideally suited for many chemical conversions, circulating solids systems have limitations restricting their usefulness in particular applications. For example, as the period between successive replenishment/regeneration and reaction steps decreases, increasingly larger amounts of solids must be moved within the system, vastly increasing the cost and complexity of the reaction system. As a further example, chemical conversions requiring relatively severe operating conditions (especially those requiring high temperatures) may adversely effect the physical or other properties of the solid, which in turn adversely effect the solid's fluidization characteristics.

Thus, despite the widespread use of fluidized bed or other moving bed systems in fluid-solid contacting, chemical conversion processes, fixed bed systems remain important to a substantial number of chemical processes. See, for example, U.S. Pat. No. 4,406,777 which describes a number of problems encountered with fixed bed reactor systems involving gradually deactivating solids and solutions proposed therefore.

In addition, when used for exothermic chemical conversions, removal of heat from fixed beds of solids is difficult without causing prohibitive temperature gradients in the reactor beds. Use of tubular reactors may overcome this difficutly, but improved systems are desirable.

3. Synthesis of Hydrocarbons From a Methane Source

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins such as ethylene or propylene would be extremely valuable to the chemical industry Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for th oxidative conversion of methane but active oxygen may be replaced by regenerating of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. patent application Ser. Nos. 522,925 now U.S. Pat. No. 4,443,649; 522,944, now U.S. Pat. No. 4,444,984; 522,942 now U.S. Pat. No. 4,443,648; 522,905 now U.S. Pat. No. 4,443,645; 522,877 now U.S. Pat. No. 4,443,647; 522,876 now U.S. Pat. No. 4,443,644; and 522,906 now U.S. Pat. No. 4,443,646, all filed Aug. 12, 1983 the entire contents of each being incorporated herein by reference.

Commonly-assigned U.S. patent application Ser. No. 522,935, filed Aug. 12, 1983 now U.S. Pat. No. 4,554,395, discloses and claims a process which comprises contacting methane with an oxidative synthesizing agent under elevated pressure (e.g., 2–100 atmospheres) to produce greater amount of $C_3+$ hydrocarbon products.

Commonly-assigned U.S. patent application Ser. No. 522,938, Aug. 12, 1983 now U.S. Pat. No. 4,560,821, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. patent application Ser. No. 522,937, filed Aug. 12, 1983 now U.S. Pat. No. 4,499,322, discloses and claims a process for the conversion of methane to higher hydrocarbons which comprises contacting methane with an oxidative synthesizing agent containing a promoting amount of alkali metal and/or compounds thereof.

Commonly-assigned U.S. patent application Ser. No. 522,936, filed Aug. 12, 1983 now U.S. Pat. No. 4,495,374, discloses and claims a process for the conversion of methane to higher hydrocarbons which comprises contacting methane with an oxidative synthesizing agent containing a promoting amount of alkaline earth metal and/or compounds thereof.

Commonly-assigned U.S. patent application Ser. No. 600,665 now U.S. Pat. No. 4,499,323, discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof.

Commonly-assigned U.S. patent application Ser. No. 600,918 now abandoned discloses and claims a process for the conversion of methane to higher hydrocarbons which comprises contacting methane with a contact solid comprising a reducible oxide of terbium and at least one member of the group consisting of alkali metals, alkaline earth metals, and compounds thereof.

Commonly-assigned U.S. patent application Ser. No. 600,917 now U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof.

4. Dehydrogenation of Hydrocarbons

Various processes for the dehydrogenation of hydrocarbons are known. Such processes seek to produce olefins and/or dienes from alkanes or to produce dienes from olefins. More conventional dehydrogenation processes include thermal or catalytic dehydrogenation. More recently, processes have been introduced. See generally McKetta, J.J., et al., *Encyclopedia of Chemical Processing and Design*, Vol. 5, pages 127-139 (Marcel Dekker, N.Y., N.Y. 1977) (discusses various dehydrogenation processes in the context of butadiene manufacturing).

In the oxidative dehydrogenation process, hydrogen is removed from a hydrocarbon by oxygen, forming water. Oxydehydrogenation catalysts have been made from a variety from metal oxides and salts.

5. Objects of the Invention

It is an object of this invention to provide a fixed bed reactor system, especially one having enhanced capabilities for the removal and utilization of heat generated by exothermic chemical conversions.

It is another object of this invention to provide an improved process for the chemical conversion of hydrocarbons.

It is a further object of this invention to provide a fixed-bed process for the synthesis of hydrocarbons from a methane source.

It is still a further object of this invention to provide a fixed-bed process for the dehydrogenation of hydrocarbons.

Other aspects, objects and the several advantages of this invention will become apparent to those skilled in the art upon reading this disclosure and the appended claims.

SUMMARY OF THE INVENTION

In accordance with the present invention, a chemical conversion process is provided wherein a reactant is contacted with fixed beds of solids to effect the desired conversion. The process is characterized by rapid deactivation of the solids (the solids functioning as a catalyst and/or a reactant), and an exothermic reactivation of the solids.

More particularly, this invention relates to an improvement in chemical conversion processes of the type wherein a reactant is contacted with a solid at an elevated reaction temperature to produce a reaction product, said solid being rapidly deactivated during said contact, and said deactivated solid being reactivated by contact with a reactivating gas under exothermic conditions and again contacted with said reactant, said improvement comprising:

(a) providing a quantity of solids in relatively equal amounts in at least three fixed bed reactors;

(b) sequentially operating each fixed bed reactor according to the cycle compriing: (1) introducing said reactant, preheated to reaction temperature, into a first end of said reactor and withdrawing reaction product from a second end of the reactor; (2) preheating said reactant to reaction temperature by introducing said reactant into said fixed bed of solids at a plurality of points along the length of said reactor and withdrawing preheated reactant from a second end of the reactor; (3) reactivating deactivated solids by introducing said reactivating gas into said fixed bed of solids at a plurality of points along the length of said reactor and withdrawing gaseous effluent from a first end of the reactor; and (c) concurrently operating said reactors such that at any given time, the reactant is being preheated to reaction temperature in a first reactor and said preheated reactant is being converted into said reaction product in a second bed.

As will be apparent to one skilled in the art it will generally be desirable to purge the reactors between the reaction and preheating steps of the cycle and between the reactivation and reaction steps of the cycle. Such is within the scope of the present invention.

In one specific embodiment of the process of this invention the chemical conversion process is a method for converting methane to higher hydrocarbon products which comprises contacting methane at a reaction temperature, preferably within the range of about 500° to 1000° C., with a quantity of solids comprising at least one reducible oxide of at least one metal which oxides are reduced when contacted with methane and produce higher hydrocarbon products and water and wherein solids comprising reduced metal oxides are periodically contacted with a oxygen-containing gas to regenerate solids comprising said reducible oxides.

In another specific embodiment of the process of this invention, the chemical conversion process is a method for dehydrogenating hydrocarbons which comprises: (1) contacting the hydrocarbon with an oxidative dehydrogenation agent to form water and dehydrogenated hydrocarbon products and (2) contacting deactivated oxidative dehydrogenation agent with an oxygen-containing gas to reactivate the In accordance with another aspect of the present invention a multi-reactor fixed bed contacting system, one embodiment of which is shown in FIG. 6, is provided which system comprises:

(a) a plurality of reactors, each adapted to contain a fixed bed of solids, each having an inlet means for introducing gaseous material into the fixed bed of solids at a plurality of points along the length of the reactor, each having an inlet/outlet means for intoducing gaseous material to a first end of the reactor and/or withdrawing gaseous material from the first end of the reactor, and each having an outlet means for withdrawing gasous material from the second end of the reactor;

(b) a first inlet manifold;
(c) a second inlet manifold;
(d) a reactor transfer manifold;
(e) a first outlet manifold:
(f) a second outlet manifold;
(g) conduit and valve means to pass flow to the inlet means of each reactor, selectively and alternatively, from:
(1) the first inlet manifold and (2) the second inlet manifold;
(h) conduit and valve means to pass flow from the outlet means of each reactor, selectively and alternatively, to: (1) the first outlet manifold and (2) the reactor transfer manifold;
(i) conduit and valve means to pass flow selectively from the reactor transfer manifold to the inlet/outlet means of each reactor and alternatively from the inlet/outlet means to the second outlet manifold.

DETAILED DESCRIPTON OF THE INVENTION

1. Chemical Conversion Process

Figure 1:
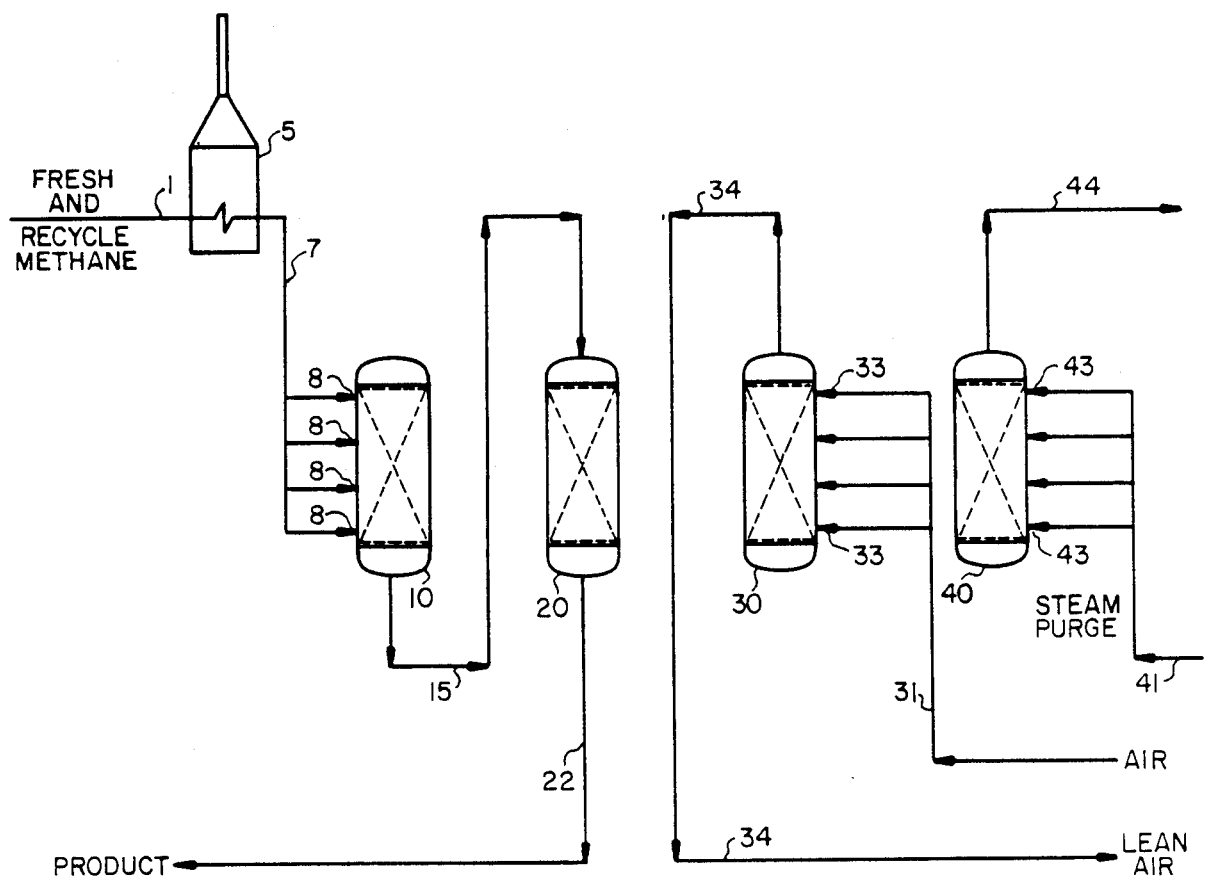
FIG. 1 is a schematic diagram showing the flow of material through a four-bed reactor module embodying the method of this invention, at a particular time in the process cycle for converting methane to higher hydrocarbons.

In its broader aspects, the process of the present invention includes improved methods for performing a variety of chemical conversions, and therefore, the following, more detailed description of specific embodiments of this broader process are intended to be illustative but not limiting of the claimed process.

As previously noted, the process is generally concerned with problems arising when fixed bed reactors are employed for a certain class of chemical conversions. One characteristic of this class is that a gaseous reactant is contacted with a solid at an elevated reaction temperature. By "elevated reaction temperature" is meant a temperature greater than ambient. More typically, the temperature will be above 200° C. The function of the solid in the conversion process is not narrowly critical. Generally however, it effects the conversion by functioning as a catalyst or as a reactant or both.

A second characteristic of the class of chemical conversions to which this invention pertains is that conversion of gaseous reactant may occur under a fairly wide temperature range without a adversely affecting non-selective reactions. The overall conversion may be endothermic or exothermic without effecting the suitability of applying the method of this invention.

A third characteristic is that the solid is deactivated during conversion of the gaseous reactant. Any process wherein the solid may be considered a reactant will fulfill this characteristic.

A fourth characteristic is that the deactivated solid is periodically contacted with a reactivating gas to reactivate the solid. It is the exothermic nature of this reactivation and the consequent non-isothermal behavior of the overall process which present a principle problem addressed by this invention: removal of heat from the fixed bed reactors without causing prohibitive temperature gradients in the reactor beds. Use of tubular reactors coupled with indirect heat exchange means has been previously employed in this context. The present invention overcomes the heat problem without the need to employ tubular reactors. In a typical application of the process of this invention, the reactivating gas will be an oxygen-containing gas but the broader embodiments of this invention are not so limited. Best applications of this process are made in conversion processes wherein solid reactivation is exothermic.

Suitable applications of the broader process of this invention will be apparent to one skilled in the art. The operation of the process and its various advantages are illustrated by its more specific embodiments.

2. Synthesis of Hydrocarbons From a Methane Source

One highly advantageous application of the general process of this invention is the conversion of methane to higher hydrocarbons. More particularly this aspect of the invention relates to an improvement in a method for converting methane to higher hydrocarbon wherein a gas comprising methane is contacted at a reaction temperature within the range of about 500° to 1000° C. with a quantity of solids comprising at least one reducible oxide of at least one metal which oxides are reduced when contacted with methane and produce higher hydrocarbon products and water and wherein solids comprising reduced metal oxides are periodically contacted with an oxygen-containing gas to regenerate solids comprising said reducible oxides, said improvement comprising:

(a) providing a quantity of solids in relatively equal amounts in at least three fixed bed reactors;

(b) sequentially operating each fixed bed reactor according to the cycle comprising: (1) introducing a gas comprising methane, preheated to reaction temperature, into a first end of said reactor and withdrawing gaseous reaction products comprising higher hydrocarbons from a second end of the reactor; (2) preheating said gas comprising methane to reaction temperature by introducing said gas into said fixed bed of solids at a plurality of points along the length of said reactor and with drawing preheated gas comprising methane from a second end of the reactor; and (3) regenerating solids comprising reducible metal oxides by introducing an oxygen-containing gas into said fixed bed of solids at a plurality of points along the length of said reactor and withdrawing gaseous effluent from a first end of the reactor; and (c) concurrently operating said reactors such that at any give time, the gas comprising methane is being preheated to reaction temperature in a first reactor, and said preheated gas comprising methane is being converted into hydrocarbon products in a second reactor.

Preferably, gas comprising methane is purged from the cooled solids after the methane preheating step and before the solids regeneration step. Also, oxygen-containing gas is preferably purged from the solids after the solids regeneration and before the methane reaction step. Purging the reactor may be easily accomplished by passing a gaseous material such as nitrogen or steam through the solids.

In addition to methane the feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof. Alakali and alkaline earth metals and compounds have been found to improve the hydrocarbon product selectivity of these agents. The further incorporation of phosphorus into agents promoted by alkali or alkaline earth components enhances catalyst stability.

Reducible oxides of cerium, praseodymium, and terbium have also been found to be effective for the conversion of methane to higher hydrocarbons when the rare earth component is associated with an alkali or alkaline earth metal component.

The metal components may be associated with other support materials such as silica, magnesia, alumina, titania, zirconia and the like and combinations thereof. When employing agents containing rare earth components—oxides of Ce, Pr and Tb—the rare earth oxides preferably serve as supports.

Reducible oxides of manganese have been found to be particularly desirable for methane conversion, especially when associated with an alkali metal (preferably sodium). Especially preferred agents comprise silica- and/or magnesia supported agents containing oxides of manganese and sodium.

The agent contacted with methane in the first step of the present invention can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkali or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solids calcined, preferably in air, at a temperature within the range of about 300° to 1200° C. Particular calcination temperatures will vary depending upon the particular metal compound or compounds employed.

Regardless of how the components of the agent are combined, the composite will be dried and calcined at elevated temperatures prior to use of the process of this invention.

Preferably, methane is contacted with the agent in the substantial absence of catalytically effective -nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the first step of this invention relative to such contacting in the absence of such metals and compounds thereof.

Operating temperatures for the first step of the method of this invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds threof) during methne contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In applying the general method of this invention to the synthesis of hydrocarbons from methane, at least one module consisting of at least three fixed bed reactors will be employed. At any given time, at least one reactor in the module is preheating methane, at least one reactor in the module is converting methane to higher hydrocarbons and at least one reactor in the module is regenerating. Other parallel modules may be provided and, within any module, other reactors may be operating at any given point in the above-described cycle.

In a preferred embodiment of this aspect of the method of the method of this invention, a module consists of four reactor units. A four-reactor module is shown in FIG. 1 with one reactor preheating methane, one reactor converting methane to higher hydrocarbons, one reactor regenerating, and one reactor being purged. The methane conversion step is slightly exothermic but the regeneration step is very exothermic. Heat is removed by feeding gas comprising methane and oxygen-containing gas to the reactor system at temperatures below reaction temperature. These feed temperatures may be adjusted to provide the desired heat balance and temperature profiles for the reactor system.

Referring now to FIG. 1, a gas comprising methane is introduced through line 1 to a heating means 5 wherein the gas may be heated to a temperature below the reaction temperature, said temperature being selected or described above. Gas passes from heating means 5 through line 7 to reactor 10 where the gas comprising methane is preheated to reaction temperature by being introduced into a bed of solids at a plurality of points 8 along the length of the reactor. Introduction will be accomplished through injection means (e.g., spargers) designed to provide dispersal of the feed gas relatively uniformly across the cross section of the solids bed at each injection point. Gas comprising methane, preheated to reaction temperature, is withdrawn from a second end of reactor 10 through line 15 and passes to a first end of reactor 20. A gaseous effluent comprising higher hydrocarbon products is withdrawn from a second end of reactor 20 through line 22. An oxygen-containing gas (e.g., air) is introduced through line 31 into the fixed bed of solids in reactor 30 at a plurality of points 33 along the length of the reactor. Gaseous effluent from the regeneration step is withdrawn from a first end of reactor 30 through line 34 for disposal. A purge gas (e.g., steam) is introduced through line 41 at a plurality of points 43 along the length of reactor 40 and purged gas is withdrawn from a first end of reactor 40 through line 44.

In FIG. 1, the reactor being purged had just been regenerated. Therefore, the purge gas is introduced and purged gas withdrawn in a manner similar to the flow of air through reactor 10. In another part of the cycle when a reactor is purged after the preheat step, the purge gas is introduced and withdrawn the same way methane was.

Figure 2:
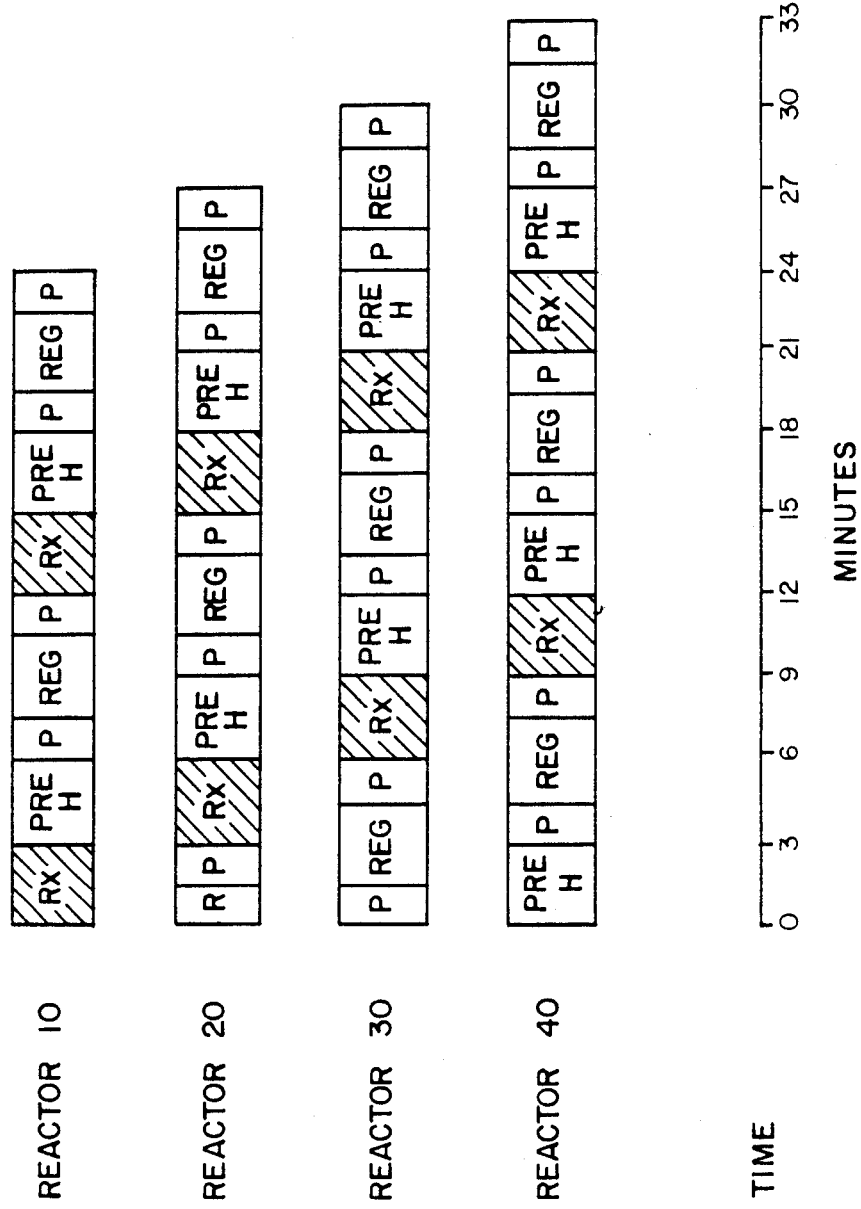
FIG. 2 shows the sequence of operations in each of the reactors of a four-reactor module being used for converting methane to higher hydrocarbons according to the method of this invention.

The sequence that each reactor in the four-reactor module goes through is shown in FIG. 2. The Figure describes a 12-minute cycle consisting of a 3-minute reaction period (designated "Rx" in the Figure), 3-minute preheat period (designed "PRE H" in the Figure), a 1½-minute purge (designated "P" in the Figure), a 3-minute regeneration period (designated "REG" in the Figure), and another 1½-minute purge. The flow will be as shown on FIG. 1 at the three-minute point on FIG. 2.

EXAMPLE

Figure 3:
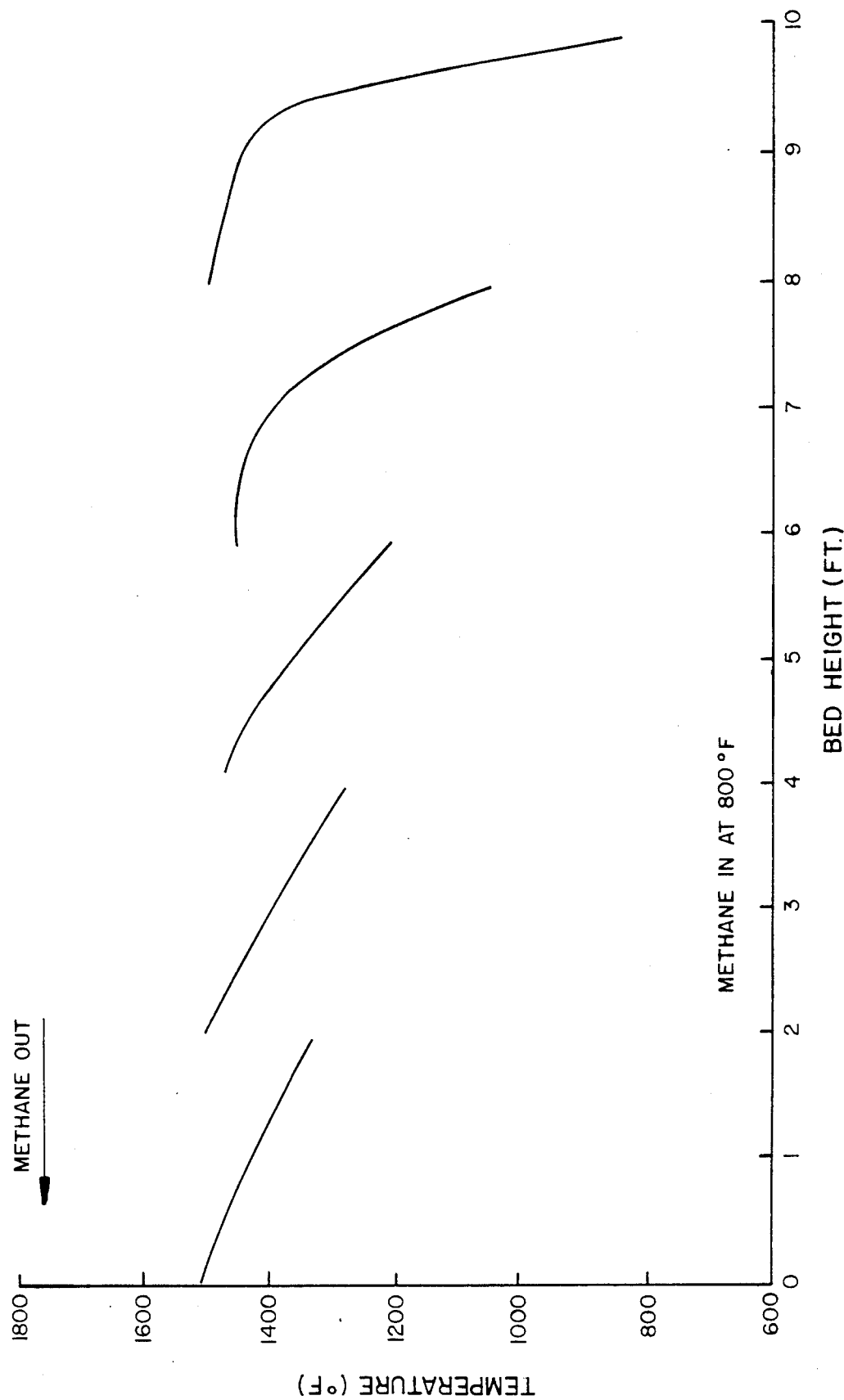
FIGS. 3–5 show reactor temperature profiles at the end of various steps of the methane, conversion process cycle, as described in the Example below.
Figure 4:
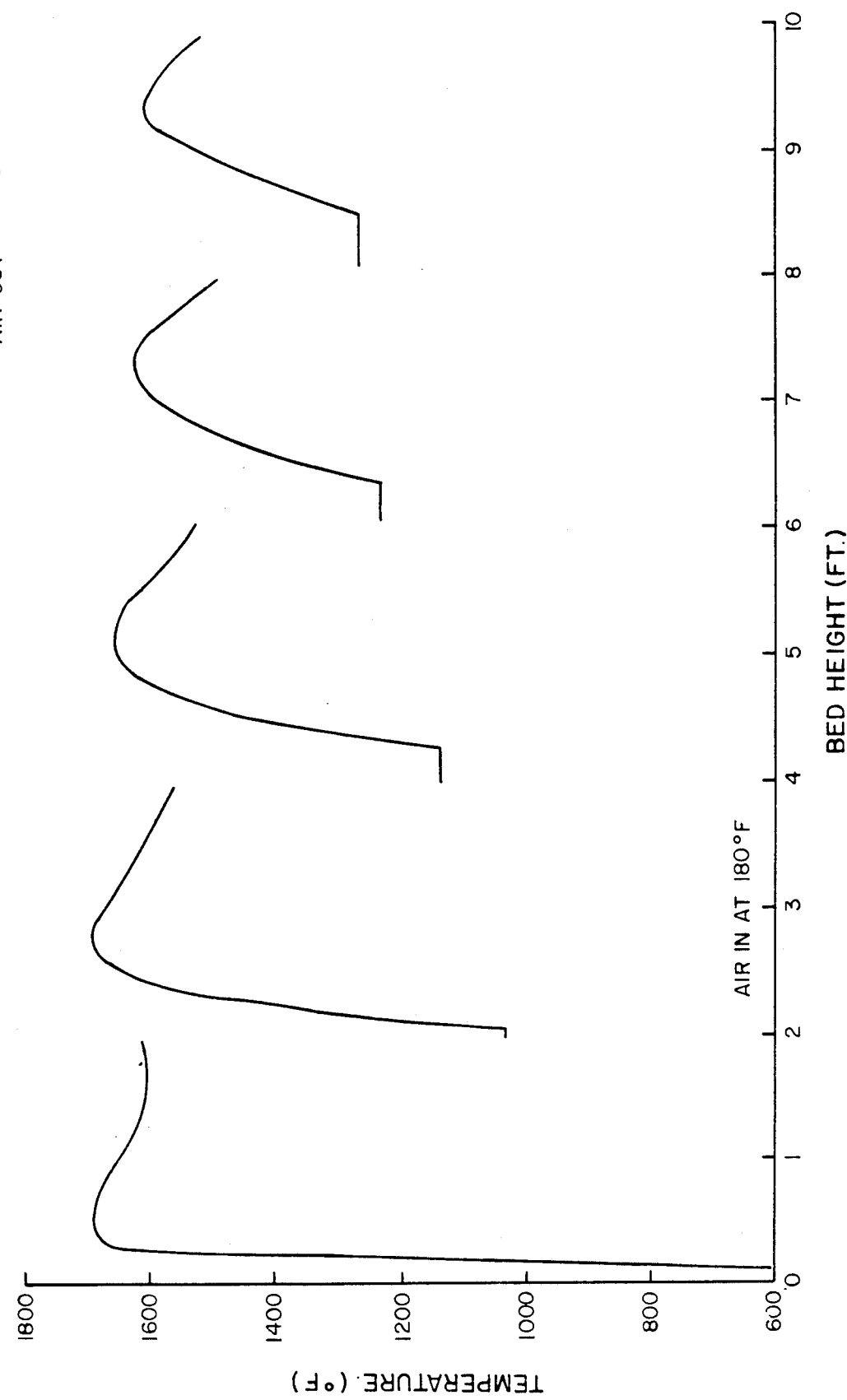
Figure 5:
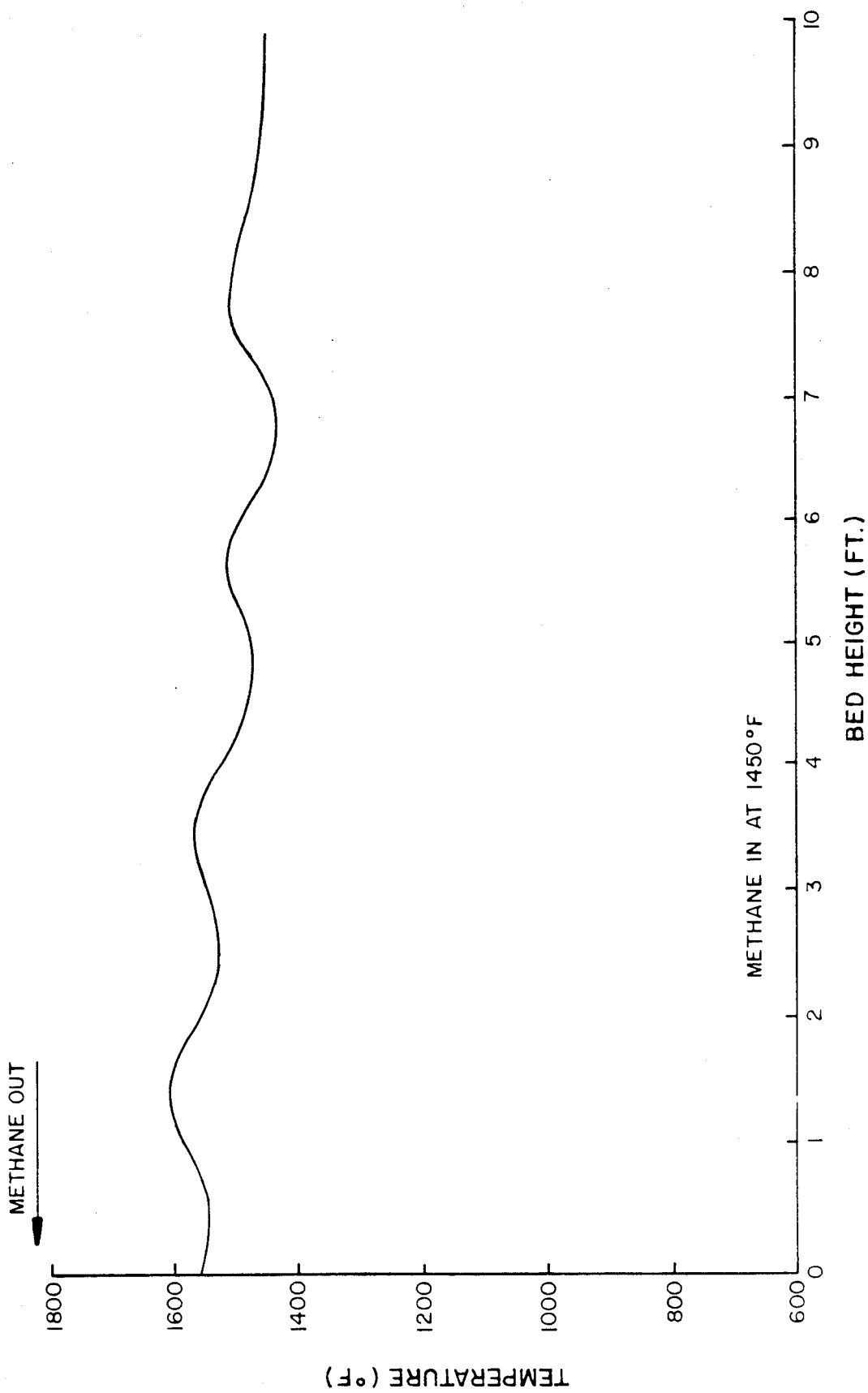

Using the four-reactor module, fixed bed system described above, a model has been developed which calculates the temperature gradient in each bed throughout the cylces of operation. This Example further assumes four identical reactors having a bed depth of 10 feet. Each reactor has a plurality of injection points spaced along the length of the reactor at points 2 feet apart. Methane feed is provided at a temperature of about 430° C. The "reaction temperature" is about 790° C. After completing five cycles of operation it was found that the temperature profiles of each fixed bed came to the same point after completion of each step of the cycle. Temperature profiles after completion of the methane preheating, methane reaction and solids regeneration steps are shown in FIGS. 3, 4 and 5, respectively. Referring to FIG. 3, the temperature profile is of a bed which has been cooled with 430° C. methane (thereby preheating the methane to reaction temperature). Referring to FIG. 4, the temperature profile is of a bed which has been reheated by passing air (introduced at about 82° C.) through each reaction injection point. Referring to FIG. 5, the temperature profile is of a bed which has been contacted with methane to effect the desired conversion. Note the relatively smooth temperature profile attained after the methane conversion step of the cycle.

3. Dehydrogenation of Hydrocarbons

Dehydrogenation of normally gaseous and light liquid hydrocarbons to less saturated hydrocarbons is a well-known process. Paraffins are dehydrogenated to produce olefins and certain olefins are dehydrogenated to produce olefins. Butadiene for example may be produced by dehydrogenating butylene from any selected source such as the butylenes obtained from the dehydrogenation of butane.

The general process of the present invention is applicable to dehydrogenation processes wherein a dehydrogentable hydrocarbon is contacted with an oxidative dehydrogenation agent (or catalyst) to produce a dehydrogenated hydrocarbon product. The catalyst may be any of a number of metal oxide or metal salt catalysts exemplified by bismuth-molybdate, magnesium-chromium-ferrite and manganese-ferrite.

Oxidative dehydrogenation agents are compositions comprising at least one oxide of at least one metal, which compositions, when contacted with a dehydrogenatable hydrocarbon (preferably at a temperature selected within the range of about 500° to 1000° C.), produces dehydrogenated hydrocarbons products, co-product water, and a composition comprising a reduced metal oxide. The composition thus contains at least one reducible oxide of at least one metal. The term "reducible" is used to identify those oxides of metals which are reduced by contact with dehydrogenatable hydrocarbons at elevated temperatures (preferably selected within the range of about 500° to 1000° C.). The term "oxide(s) of metal(s)" includes (1) one or more metal oxides (i.e., compounds described by the general formula $M_xO_y$ wherein M is a metal and the subscripts $x$ and $y$ designate the relative atomic proportions of metal and oxygen in the compound) and/or (2) one or more oxygen-containing metal compounds, provided that such oxides and compounds have the capability of performing to dehydrogenate dehydrogenatable hydrocarbons as set forth herein.

One class of preferred oxidative dehydrogenation agents comprises reducible oxides of metals selected from the group consisting of Mn,Sn,In,Ge,Sb,Pb, Bi, and mixtures thereof. Particularly preferred oxidative dehydrogenation agents comprise a reducible oxide of manganese and mixtures of reducible oxides of manganese with other oxidative dehydrogenation agents. More particularly preferred are reducible oxides of manganese associated with a silica support. See concurrently filed U.S. patent application Ser. No. 600,916, the entire content of which is incorporated herein by reference.

Another class of preferred oxidative dehydrogenation agents comprise a reducible metal oxide and a promoting amount of an alkali and/or alkaline earth metal component. A particularly preferred member of this class of agents comprises a reducible metal oxide and a promoting amount of an alkali metal associated with a support comprising an alkaline earth metal and/or compound thereof. More particularly preferred are solids comprising a reducible oxide of Mn, Na and/or a compound thereof, and a support comprising magnesia See concurrently filed U.S. patent application Ser. No. 600,655 now abandoned, the entire content of which is incorporated herein by reference.

Still another class of preferred oxidable dehydrogenation agents comprises: (1) reducible oxides of metals selected from the group consisting of Pr, Tb and Ce, and (2) at least one member of the group consisting of alkali metals, alkaline earth metals and compounds thereof. See concurrently filed U.S. patent application Ser. Nos. 600,735, 600,652 now U.S. Pat. No. 4,511,754 and 600,651 now U.S. Pat. No. 4,560,823, the entire contents of which are incorporated herein by reference. Reducible oxides of Pr and Tb are particularly preferred members of this class of agents. Reducible oxides of Pr -are still more particularly preferred. Especially preferred members of this class are agents wherein the said reducible oxides are provided as supports for the other components of the agent.

A still further class of preferred oxidative dehydrogenation agents comprises: (1) reducible oxides of metals selected from the group consisting of Fe and Ru and (2) at least one member of the group consisting of alkali metals, alkaline earth metals and compounds thereof. See concurrently filed U.S. patent application Ser. Nos. 600,734 now abandoned and 600,736, now U.S. Pat. No. 4,568,789, the entire contents of which are incorporated herein by reference. Reducible oxides of Fe are, currently, a particularly preferred member of this class of agents. Also particularly preferred are agents wherein the said reducible oxides are provided as supports or the other components of the agent.

Other oxidative dehydrogentation agents may also be employed in the method of this invention, as will be apparent to one skilled in the art.

In the present invention, reducible oxides are provided as solid particles. They may be supported by, or diluted with, a conventional support material such as silica, alumina, titania, zirconia, and the like, and combinations thereof. A presently preferred support is silica.

Supported solids (i.e., particles) can be prepared by any suitable method. Conventional methods such as adsorption, impregnation, precipitation, coprecipitation, or dry-mixing can be used. A suitable method is to impregnate the support with solutions of compounds of the desired metal. Some examples of suitable compounds are the acetate, acetylacetonate, oxide, carbide, carbonate, hydroxide, formate, oxalate, nitrate, phosphate, sulfate, sulfide, tartrate, fluoride, chloride, bromide or iodide. After impregnation, the preparation is dried in an oven to remove solvent and the dried solid is prepared for use by calcining, preferably in air, at temperatures selected within the range of about 300° to 1200° C. Particular calcination temperatures will vary depending upon the particular metal compound.

Metal loadings on supported solids will generally be within the range of about 1 to 50 wt. % (calculated as the elemental metal(s) of the reducible oxides(s)).

The dehydrogentable hydrocarbon feedstock employed in the method of this invention is intended to include a wide variety ot hydrocarbons; e.g., $C_2+$ alkanes, cycloalkanes, olefins, alkylaromatics, etc. The dehydrogenated product will of course depend in part on the feedstock selected. For example, alkanes may be dehydrogenated to form olefins, diolefins, alkynes, etc., and olefins may be dehydrogenated to form diolefins, alkynes, etc. Thus, potential uses for the present process include the following conversions:

(1) ehtane→ethylene→acetylene;
(2) propane→propylene;
(3) butane→butene→butadiene;
(4) 2-methylbutane→2-methylbutenes→isoprene; and
(5) toluene→stilbene.

One preferred class of feedstocks comprises $C_2$-$C_5$ alkanes.

Operating temperatures for the contacting of hydrocarbon-containing gas and the particles comprising an oxidative dehydrogenating agent are preferably selected from the range of about 500° to 1000° C., the particular temperature selected depending upon the metal oxides employed in the oxidative dehydrogenation agent. For example, all oxidative dehydrogenation (defined above) agents have the capability of dehydrogenating hydrocarbons when the temperature of the hydrocarbon contact is selected within the lower part of the recited range. Reducible oxides of certain metals, however, may require operating temperatures below the upper part of the recited range to minimize sublimation or volatilization of the metals (or compounds thereof) during hydrocarbon contact. Examples are: (1) reducible oxides of indium (operating temperatures will preferably not exceed about 850° C.); (2) reducible oxides of germanium (operating temperatures will preferably not exceed about 800° C.); and (3) reducible oxides of bismuth (operating temperatures will preferably not exceed about 850° C.).

Operating pressures for the hydrocarbon contacting step are not critical to the presently claimed invention.

Contacting hydrocarbon and an oxidative dehyrogenation agent to dehyrogenate dehydrogenatable hydrocarbons also reduces the oxidative dehydrogenation agent and produces coproduct water. The exact nature of the reduced forms of oxidative dehydrogenation agents are unknown, and so are referred to herein as "reduced dehydrogenation agent" or as "a reduced metal oxide." Regeneration of a reducible metal oxide is readily accomplished by contacting reduced compositions with oxygen (e.g., an oxygen-containing gas such as air) at a temperature selected within the range of about 300° to 1200° C., the particular temperature selected depending on the metal(s) included in the oxidative dehydrogenation agent.

In applying the general method of this invention to the dehydrogenation of dehydrogenatable hydrocarbons, at least one module consisting of at least three fixed bed reactors will be employed. At any given time, at least one reactor in the module is preheating hydrocarbons, at least one reactor in the module is dehydrogenating hydrocarbons to dehydrogenated hydrocarbons and (preferably) at least one reactor in the module is regenerating. Other parallel modules may be provided and, within any module, other reactors may be operating at any given point in the abovedescribed cycle. Operation of the reactor system to dehydrogenate hydrocarbons is analogous to the methane conversion process already described. Since the dehydrogenation reactions may be more endothermic than the methane conversion reactions, higher preheat temperatures for dehydrogenatable hydrocarbons may be desirable. Also, because of different relative reaction rates of the hydrocarbon contacting step and the regeneration step, a different number of reactors per module and different cycle times may be desirable for hydrocarbon dehydrogenation.

4. Multi-Reactor Fixed Bed Gas-Solid Contacting System

This aspect of the present invention is illustrated below by reference to a reactor system of four beds. However, this is for purposes of illustration only. Any number of reactors may be incorporated into the system, as will be apparent to those skilled in the art. Also, for purposes of illustration, an embodiment of the reactor apparatus will be illustrated in the context of a methane conversion process, as described more fully above.

Figure 6:
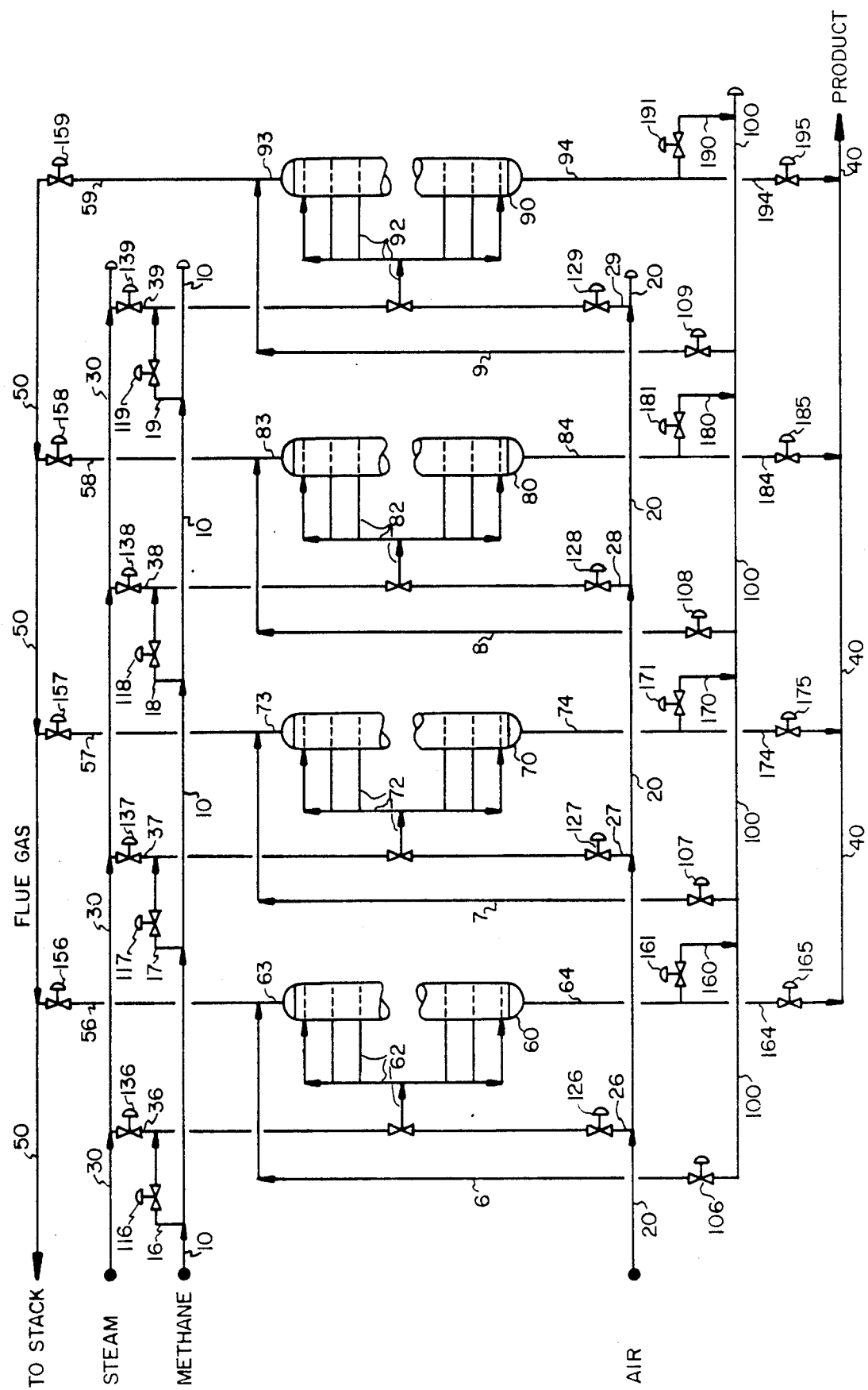
FIG. 6 is a schematic diagram of one embodiment of the multi-reactor, fixed bed, gas-solid contacting system of this invention.

Referring now to FIG. 6, fixed beds of solids are provided in relatively equal amounts in reactors 60, 70, 80 and 90. Each of the reactors has an inlet means for introducing gaseous material into the fixed bed of solids at a plurality of points along the length of the reactor. Such inlet means are generally designated in the Figure as 62, 72, 82 and 92 for reactors 60, 70, 80 and 90, respectively. Each of the reactors also has an inlet/outlet means for introducing gaseous material to a first end of each reactor and/or withdrawing gaseous material from a first end of each reactor. Such inlet/outlet means are designated in the Figure as conduits 63, 73, 83 and 93 for reactors 60, 70, 80 and 90, respectively. Each of the reactors also has an outlet means for withdrawing gaseous material from a second end of the reactors. Such outlet means are designated as conduits 64, 74, 84 and 94 for reactors 60, 70, 80 and 90, respectively.

A gas comprising methane is provided to the reactor system through a first inlet manifold 10. An oxygen-containing gas is provided to the reactor system through a second inlet manifold 20. Purge gas is provided through a third inlet manifold 30. The purge gas is indicated to comprise steam in the FIG. 6.

Conduit and valve means are provided to pass flow to inlet means 62, 72, 82 and 92, selectively and alternatively, from: (1) inlet manifold 10, (provides a gas comprising methane), (2) inlet manifold 20 (provides an oxygencontaining gas) and (3) inlet manifold 30 (provides an optional purge gas). Such conduit and valve means for reactor 60 are shown in FIG. 6 as follows: conduit 16 and valve 116 for said selective and alternative flow relationship between inlet manifold 10 and inlet means 62; conduit 26 and valve 126 for said selective and alternative flow relationship between inlet manifold 20 and inlet means 62; and conduit 36 and valve 136 for said selective and alternative flow relationship between inlet manifold 30 and inlet means 62. The conduit and valve means schematically illustrated in FIG. 6 are illustrative. For example other valve means, such as, the use of three-way valves may be employed. Similar conduit and valve means are shown for reactors 70, 80 and 90 in a manner analogous to reactor 60.

Conduit and valve means are also provided to pass flow selectively from outlet means 64, 74, 84 and 94 to a reactor transfer manifold 100 and alternatively to the first outlet manifold 40. The first outlet manifold 40, in the process embodiment shown, receives effluent from each reactor during the methane conversion portion of its process recycle. The reactor transfer manifold 100 collects preheated methane from each of the reactors and provides preheated methane feed to each reactor during the methane conversion portion of its process cycle. The conduit and valve means provided to pass flow selectivity from the outlet means 64 of reactor 60 to reactor transfer manifold 100 and alternatively to outlet manifold 40 are shown in FIG. 6 as follows: conduit 160 and valve 161 for said selective and alternative flow relationship between outlet 64 and manifold 100 and conduit 164 and valve 165 for said selective and alternative flow relationship between outlet 64 and manifold 40. Similar conduit and valve means are shown for reactors 70, 80 and 90 in a manner analogous to reactor 60.

Conduit and valve means are also provided to pass flow selectively from the reactor transfer manifold 100 to inlet/outlet means 63, 73, 83 and 93 and alternatively from inlet/outlet means 63, 73, 83 and 93 to the second outlet manifold 50.

The second outlet manifold 50, in the process embodiment shown, receives effluent from each reactor during the regeneration portion of its process cycle. The manifold 50 may also receive gas purged from the fixed beds of each reactor during the purge following the regeneration step.

The reactor transfer manifold 100 receives preheated methane feed from each reactor during the methane preheat portion of its process cycle, as described above, and provides preheated methane feed to each reactor during the methane conversion portion of its process cycle. The conduit and valve means provided to pass flow selectively from the reactor transfer manifold 100 to inlet/outlet means 63 of reactor 60 and alternatively to pass flow selectively from inlet/outlet means 63 to second outlet manifold 50 are shown in FIG. 6 as follows: conduit 6 and valve 106 for said selective and alternative flow relationship between reactor transfer manifold 100 and inlet/outlet means 63 and conduit 56 and valve 156 for said selective and alternative flow relationship between inlet/outlet means 63 and outlet manifold 50. Similar conduit and valve means are shown for reactors 70, 80 and 90 in a manner analogous to reactor 60.

To exemplify the use the foregoing apparatus for the conversion of methane, consider the form of FIG. 6 apparatus at a point in the overall process cycle which corresponds to that shown in FIG. 1. Methane feed from manifold 10 is introduced through line 16 to inlet means 62 of reactor 60. Valve 116 is open. Valves 117, 118 and 119 are closed. Also, valves 126 and 136 are closed. Methane introduced into the fixed bed of solids (comprising reduced metal oxides) contained in reactor 60 at a plurality of point along the length of the reactor is preheated to reaction temperature and withdrawn through lines 64 and 160 to reactor transfer manifold 100 and from there through line 7 to inlet/outlet means 73 of reactor 70. Valves 161 and 107 are open. Valves 171, 181 and 191 are closed, as are valves 165, 185 and 195 and valves 106, 108 and 109. The methane feed, preheated to reaction temperature, passes through the fixed bed of solids (comprising reducible metal oxides) contained in reactor 70 and a gaseous effluent comprising higher hydrocarbons is withdrawn through outlet means 74 of reactor 70 through line 174 to the first outlet manifold 40. Valve 175 is open.

Regeneration gas (e.g., air) from manifold 20 is introduced through line 28 to inlet means 82 of reactor 80. Valve 128 is open. Valves 126, 127 and 129 are closed, as are valves 118 and 138. The oxygen-containing, regeneration gas is introduced into the fixed beds of solids (initially, at the start of this portion of the cycle, comprising cooled, reduced metal oxides) contained in reactor 80 at a plurality of points along the length of the reactor to regenerate solids comprising reducible metal oxides (a highly exothermic reaction). Gaseous effluent during solids regeneration (referred to in FIG. 6 as "flue gas") is withdrawn from reactor 80 through inlet/outlet means 83 and passes via line 58 to the second outlet manifold 50. Valve 158 is open. Valves 156 and 157 are closed.

Purge gas (e.g., steam) from manifold 30 is introduced through line 39 to inlet means 92 of reactor 90. Valve 139 is open. Valves 136, 137 and 138 are closed. Purged gas is withdrawn from reactor 90 through inlet/outlet means 93 and passes via line 59 to the second outlet manifold 50. Valve 159 is open.

What is claimed is:

1. A multi-reactor, fixed bed, gas-solid contracting system comprising:
    (a) a plurality of reactors, each containing a fixed bed of solids, each having an inlet means for introducing gaseous material into the fixed bed of solids at a plurality of points along the length of the reactor, each having an inlet/outlet means for introducing gaseous material to a first end of the reactor and/or withdrawing gaseous material from the first end of the reactor, and each having an outlet means for withdrawing gaseous material from a second end of the reactor;
    (b) a first inlet manifold;
    (c) valve and conduit means positioned between said first inlet manifold and said inlet means of each reactor to provide alternative and selective flow from said first inlet manifold to each reactor;
    (d) a second inlet manifold;
    (e) valve and conduit means positioned between said second inlet manifold and said inlet means of each reactor to provide alternative and selective flow from said second inlet manifold to each reactor;
    (f) a reactor transfer manifold;
    (g) valve and conduit means positioned between said reactor transfer manifold and said outlet means of each reactor to provide alternative and selective flow from each reactor to said transfer manifold;
    (h) valve and conduit means positioned between said reactor transfer manifold and said inlet/outlet means of each reactor to provide alternative and selective flow from said transfer manifold to said inlet/outlet means of each reactor;
    (i) a first outlet manifold;
    (j) valve and conduit means positioned between said outlet means of each reactor and said first outlet manifold to provide alternative and selective flow from said outlet means of each reactor to said first outlet manifold;
    (k) a second outlet mainfold;
    (l) valve and conduit means positioned between said inlet/outlet means of each reactor and said second outlet manifold to provide alternative and selective flow from said inlet/outlet means of each reactor to said second outlet manifold; structure being provided for said system such that said system is capable of at any one time (1) providing flow form said first inlet manifold to the said inlet means of a reactor and from said outlet means of the same reactor to said reactor transfer manifold, (2) providing flow from said reactor transfer manifold to said inlet/outlet means of a second reactor and from said outlet means of said second reactor to said first outlet manifold, and (3) providing flow from said second inlet manifold to said inlet means of a third reactor and from the said inlet/outlet means of said third reactor to said second outlet manifold.

2. A multi-reactor, fixed bed, gas-solid contacting system comprising:
    (a) a plurality of reactors, each containing a fixed bed of solids, each having an inlet means for introducing gaseous material into the fixed bed of solids at a plurality of points along the length of the reactor, each having an inlet/outlet means for introducing gaseous material to a first end of the reactor and/or withdrawing faseous material from the first end of the reactor, and each having an outlet means for withdrawing gaseous material from a second end of the reactor;
    (b) a first inlet manifold;
    (c) valve and conduit means positioned between said first inlet manifold and said inlet means of each reactor ot provide alternative and selective flow from said first inlet manifold to each reactor:
    (d) a second inlet manifold;
    (e) valve and conduit means positioned between said second inlet manifold and said inlet means of each reactor to provide alternative and selective flow from said second inlet manifold to each reactor;
    (f) a third inlet manifold;
    (g) valve and conduit means positioned between said third inlet manifold and said inlet means of each reactor to provide alternative and selective flow from said third inlet manifold to each reactor;
    (h) a reactor transfer manifold;
    (i) valve and conduit means positioned between said reactor transfer manifold and the said outlet means of each reactor to provide alternative and selective flow from each reactor to said transfer manifold;
    (j) valve and condiut means positioned between said reactor transfer manifold and said inlet/outlet means of each reactor to provide alternative and selective flow from said transfer manifold to said inlet/outlet means of each reactor;
    (k) a first outlet manifold;
    (l) valve and conduit means positioned between said outlet means of each reactor and said first outlet manifold to provide alternative and selective flow from said outlet means of each reactor to said first outlet manifold;
    (m) a second outlet manifold;

(n) valve and conduit means positioned between said inlet/outlet means of each reactor and said second outlet manifold to provide alternative and selective flow from said inlet/outlet means of each reactor to said second outlet manifold; structure being provided for said system such that said system is capable of at any one time (1) providing flow from said first inlet manifold to the said inlet means of a reactor, and from said outlet means of the same reactor to said reactor transfer manifold, (2) providing flow from said reactor transfer manifold to said inlet/outlet means of a second reactor and from said outlet means of said second reactor to said first outlet manifold, (3) providing flow from said second inlet manifold to said inlet means of a third reactor and from the said inlet/outlet means of said third reator to said second outlet manifold, and (4) providing flow from said third inlet manifold to said inlet means of a fourth reactor and from said inlet/outlet means of said fourth reactor to said second outlet manifold.

* * * * *